United States Patent [19]
Korol

[11] Patent Number: 4,747,845
[45] Date of Patent: * May 31, 1988

[54] SYNTHETIC RESIN MATRIX SYSTEM FOR THE EXTENDED DELIVERY OF DRUGS

[75] Inventor: Bernard Korol, St. Louis, Mo.

[73] Assignee: Enquay Pharmaceutical Associates, Boca Rotan, Fla.

[*] Notice: The portion of the term of this patent subsequent to Jan. 7, 2003 has been disclaimed.

[21] Appl. No.: 815,874

[22] Filed: Jan. 3, 1986

Related U.S. Application Data

[63] Continuation-in-part of Ser. No. 542,754, Oct. 17, 1983, Pat. No. 4,563,184.

[51] Int. Cl.$^4$ ............... C08K 5/41; C08K 5/34; C08K 5/15; C08K 5/10; A61L 15/01; A61L 15/06; A61L 15/03

[52] U.S. Cl. ............... 604/368; 514/708; 514/709; 514/936; 514/946; 514/965; 523/111; 523/122; 524/104; 524/111; 524/167; 524/173; 524/233; 524/296; 524/317; 128/156; 128/334 R; 128/335.5; 424/443; 424/447; 424/487

[58] Field of Search ............... 424/19, 26, 28; 514/708, 709, 936, 946, 965; 524/104, 111, 167, 173, 233, 296, 317; 523/111, 122; 604/368; 128/156, 334, 335.5

[56] References Cited

U.S. PATENT DOCUMENTS 3,954,959  5/1976  Pedersen ............... 424/21
4,111,202  9/1978  Theeuwes ............... 424/19
4,160,452  7/1979  Theeuwes ............... 424/19
4,557,755 12/1985  Takahashi et al. ............... 424/19

*Primary Examiner*—Delbert R. Phillips
*Assistant Examiner*—Nathan M. Nutter
*Attorney, Agent, or Firm*—Paul M. Denk

[57] ABSTRACT

A synthetic resin matrix system for the delayed and extended duration delivery of drugs to humans and animals is disclosed consisting of a polymer, such as poly(2-hydroxyethylmethacrylate), referred to as PHEMA, an organic solvent, such as polyethylene glycol (PEG), and a hydrogen binding plasticizer, such as dimethylsulfoxide (DMSO). The plasticizer regulates the set-up time of the synthetic resin so that the more plasticizer present, the shorter the set-up time. The plasticizer also has a direct shortening effect upon the cure time and also profoundly influences many of the physical characteristics of the resultant synthetic resin matrix system. A variety of drugs can be embodied in the fabricated matrix system and administered to the patient (or animal) by different modes of application, including but not limited to oral, topical, rectal, subcutaneous implant, or organ-specific implant such as in the conjunctival sac of the eye. These formulations and procedures can also be utilized in the storage and extended-duration delivery of agricultural products, particularly herbicides, insecticides, and nutritional supplements. By manipulating the relative concentrations of the components of the matrix system and the particle size of the embedded active agent, it is possible to control the release dynamics of the active embodied agent from the matrix and thus provide unique controlled delayed and extended delivery of the active agent.

7 Claims, 1 Drawing Sheet

U.S. Patent  May 31, 1988  4,747,845
FIG. 1.
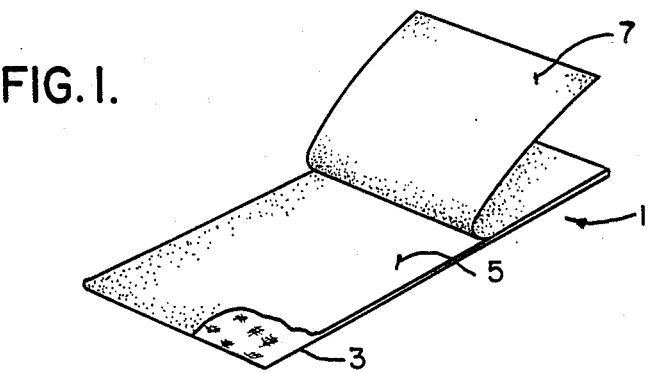
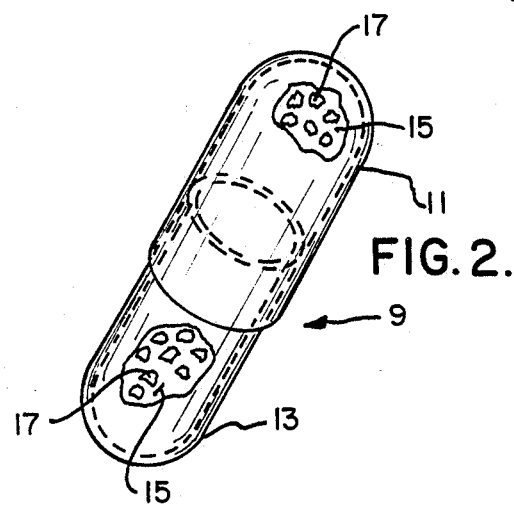
FIG. 2.
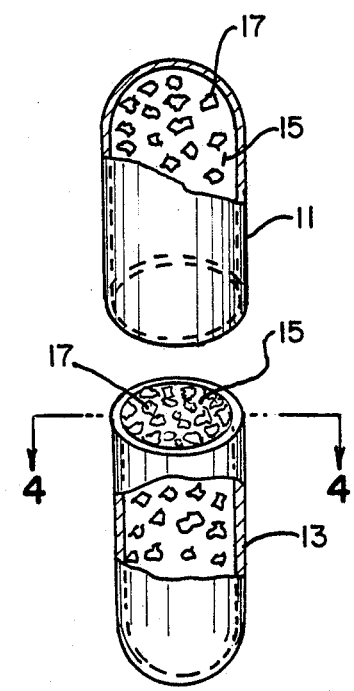
FIG. 3.
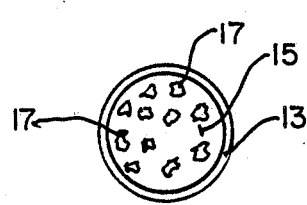
FIG. 4.
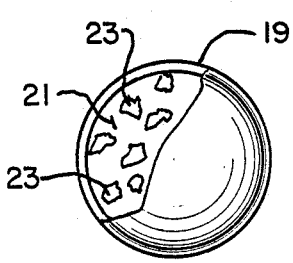
FIG. 5.
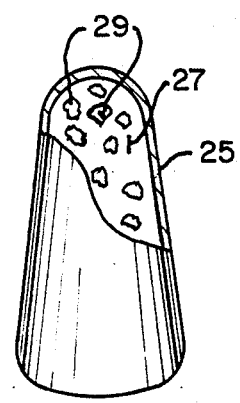
FIG. 6.

SYNTHETIC RESIN MATRIX SYSTEM FOR THE EXTENDED DELIVERY OF DRUGS

CROSS REFERENCE TO RELATED APPLICATION

This application is a continuation-in-part of the patent application of Bernard Korol, Ser. No. 542,754, filed on Oct. 17, 1983 and now U.S. Pat. No. 4,563,184.

BACKGROUND OF THE INVENTION

This invention relates to a synthetic resin matrix system which can be embodied with select drugs and chemicals and provide suitable storage for extended and sustained duration release of the embodied agent from the matrix system following various modes of administration.

According to the literature (Madan, Pharmaceutical Manufacturing, April, 1985), approximately fifty major pharmaceutical companies are engaged in the production and marketing of about 200 sustained-release drug delivery products which represent about five percent of the total pharmaceutical products sold. A survey of this literature shows that various methods have been used to fabricate these drug products. Most of the methods develop a series of protective layers of inert substance which encapsulate the drug and utilize dissolution as the rate-limiting step in controlling the release of the active ingredient from the dosage form. Because a drug form with a low dissolution rate of the overlay is slowly released, the main thrust of the development of sustained-release delivery systems has been directed toward drugs that are highly water soluble. However, the solubility of such drugs can be changed by several methods.

Orally administered extended release drug delivery systems presently available or under development employ a variety of release mechanisms ranging from: (1), enteric coating; (2), beads or spheres; (3), enteric coated beads or spheres; (4), repeat action tablets; (5), mixed release granules; (6), erosion cores, with and absent of initial dose; (7), ion exchange; (8), microencapsulation; (9), the osmotic pump; and (10), matrix tablets.

Blank and Fertig (U.S. Pat. No. 3,927,206), disclosed that copolymers comprising acrylic or methacrylic acid and methyl methacrylate, neutralized by the addition of cyclic alkylene imines, preferably ethylene imine, form a product which is capable of absorbing large amounts of material soluble in water, and slowly releasing those materials. The treated copolymers are particularly useful in the formation of contact lenses for the application of medicinals to the eye and for other depot materials.

Pedersen (U.S. Pat. No. 3,954,959), claimed an oral drug preparation having a protracted effect and a substantially constant rate of release of the drug, comprising an admixture of a drug and an effective amount of a buffer acid, buffer acid salts, and mixtures thereof, in the form of small spheroidal particles of 0.1 to 5.0 mm diameter, said particles having a coating thereon of an acrylic polymer film permitting drug diffusion. The dragee lacquer, thus formed, allows for diffusion of the stomach and intestinal juices through the coating, the coating not being soluble in said juices.

SUMMARY OF THE INVENTION

The synthetic resin matrix system of the parent invention (see U.S. patent application serial No. 542,754 now U.S. Pat. Np. 4,563,184) has been given the acronym "DIMAC", which represents the chemical components of the drug carrier and delivery system, comprised of a particulate, hydrophilic, water swellable polymer; an inert, non-toxic water miscible organic solvent; and a hydrogen bonding plasticizer; having the active drug embodied within and throughout the matrix by adding the drug while mixing the components. The potential of DIMAC to serve as a matrix for drug storage and sustained drug delivery was realized by the chance observation that the addition of the hydrogen bonding plasticizer, dimethylsulfoxide, to the formulation containing only the polymer, poly(2-hydroxyethylmethacrylate), and the organic solvent, polyethylene glycol-400, produced a synthetic polymer matrix system which exhibited essential and significant improvements in physical and functional characteristics over prior related products. the selected solvent may have a molecular weight averaging between about 200–2,000 gram molecules weight units. The DIMAC was shown to release embodied drugs in an extended duration pattern.

DIMAC, readily embodied structurally different antimicrobial agents, and released the active drug when placed upon a bacteria contaminated wound site. Thus, the DIMAC/drug products initially envisioned, developed, and evaluated for clinical utility were impregnated with anitmicrobial agents, and were designed to serve as topical applied sustained duration (days) antimicrobial delivery systems. These preparations were effective in the extended duration treatment of infected wounds. Importantly, the DIMAC system also acted as a bacterial barrier that protected the wound from further environmental contaminants.

Evidence collected supported the premise that drug release from the DIMAC matrix is primarily controlled by the nature of the environment in contact with the DIMAC/drug system. In-vitro and in-vivo studies were performed on DIMAC/drug formulations prepared as a wound dressing. It was observed that the drug release from the DIMAC matrix is facilitated by an aqueous environment. The application of the DIMAC/drug wound dressing to wound sites, agar, or cadaveric skin, revealed that the amount and duration of drug release from the DIMAC matrix was dependent upon the relative concentration of the drug in the DIMAC matrix and the thickness of the matrix gel pad. It was observed from the evaluations of these storage and release systems that high levels of active agent could be released from the DIMAC matrix for as long as several weeks. Many drugs have been evaluated and the results demonstrate that a variety of agents may be stored and topically released from the DIMAC matrix over an extended duration, e.g., when in a wound dressing configuration. These drugs include silver sulfadiazine, nitrofurazone, hydrocortisone, hydrocortisone acetate, and hydrocortisone sodium succinate.

DIMAC containing nitroglycerine was observed to release embodied nitroglycerine after feeding to a test rabbit. This particular animal exhibited high levels of plasma nitroglycerine radioactivity for many hours after consuming the DIMAC loaded with nitroglycerine, thus indicating substantial release of nitroglycerine from the DIMAC matrix throughout the gastrointestinal tract. This observation warranted future development and evaluation of the effectiveness and potential utility of DIMAC as a carrier matrix for drugs or chemicals to be administered by routes other than topical. These preparations provide an extended duration release resulting in the desired pharmacotherapeutic effectiveness.

Studies have been performed examining the storage capability and the release rates of various drugs from DIMAC matrix, in a capsular configuration and administered orally to conscious dogs. The results of these studies show that DIMAC synthetic resin matrix system serves as an effective drug storage device and releases the embodied drug in an extended duration pattern.

The synthetic resin matrix system for drug storage and extended duration drug release of this invention does include a medicament agent for local or systemic therapeutic effects, such medicament agents as selected from the pharmacological classes of drugs such as antimicrobial, antibiotic, analgesic, anticonvulsant, antipsychotic, hormone, antihistamine, cardiovascular, anxiolytic, antispasmodic, skeletal muscle relaxant, antiviral, antineoplastic, diuretic, antiparasitic, healing enhancer, respiratory, and learning and memory enhancers. The drug storage and extended duration drug release as defined herein can be used for administering such medicaments, within the matrix system, to ailing animals or humans, and by one of the many different modes of application including delivery by means of oral, rectal, topical, sublingual, subcutaneous implant, and organ specific implacement.

The synthetic resin matrix system for chemical storage and extended duration release as defined as invention herein, allows for the administration of the matrix containing various agricultural treatment products, such as herbicides, insecticides, or even nutritional supplements for application to the farm or other animal.

Hence, it is the object of the present invention to provide new configurations of synthetic resin matrix systems to be embodied with selected pharmaceutical and chemical agents and thus have the synthetic resin matrix serve as an efficient storage reservoir, and also for the synthetic resin matrix drug/chemical system to release the embodied agent at a predetermined extended duration rate following introduction of the matrix system to the treatment site.

EXAMPLE 1

Here, a preparation of the synthetic resin matrix system of the present invention embodied with an active cardiovascular medicament was prepared, wherein the medicament nitroglycerine was mixed with the paste, and wherein the nitroglycerine was present in a concentration of ten percent (10%) by weight of the PEG solvent. An experiment was performed examining nitroglycerine release from DIMAC matrix, and pentration through the abdominal skin or rabbits. The nitroglycerine was tagged with C14 as an indicator for drug absorption.

Formulation and Application:

Four DIMAC matrix pads with nitroglycerine were prepared, each matrix pad weighing approximately 4.5 grams, and containing the following component concentrations:

| DMSO | PEG-400 | NTG (cold) | PHEMA | C-14 NTG |
|------|---------|------------|-------|----------|
| 15.0% | 48.0% | 2.0% | 35.0% | 28 uCi/gm |

DIMAC matrix embodied with nitroglycerine was prepared by pouring the mixture slurry into aluminum foil cups having the dimensions of:

| 50.8 mm (2.0) inches) (diameter) | 1.5 mm in depth |
|---|---|
| Area = 20.62 cm sq. | Volume = 3.04 cm cubed |

Aluminum foil sheet was placed over the poured slurry, overlapped and cringed to the sides of the cup providing a complete seal. A glass plate, mounted on 1.5 mm shims was placed on top of the filled and sealed cups. Set-up and cure of the matrix gel to form a solid was allowed to proceed overnight.

To apply the DIMAC matrix containing nitroglycerine, the top aluminum foil cover sheet was removed and the matrix pad was placed firmly onto the skin surface on the abdominal area of the rabbit. An Adhesive Overlay Ring No. 15707, or appropriate tape, was placed over the aluminum cup and applied firmly to the skin surface of the animals. The adhesive covering kept the matrix pads edges from becoming dislodged from the skin. Additionally, the inherent adhesiveness of the DIMAC matrix pad ensured excellent continual skin contact and adherence for several days.

Results:

The C14 nitroglycerin plasma levels peaked at the 1-hour post-application sampling time and gradually returned toward the baseline, reaching pretreatment baseline level (background) at the 6-hour sampling time. Between the 6-hour and 24-hour measurement times, one of the rabbits freed and consumed a portion of the DIMAC matrix embodied with nitroglycerine. It was of considerable interest to note that the ensuing 24-hour and 32-hour post-application plasma samples from this rabbit exhibited plasma radioactivity levels ten (10) times greater than the peak effects observed earlier, with little decline in plasma radioactivity level between the 24- and 32-hour sampling times.

Conclusions:

Application to the skin surface with DIMAC containing nitroglycerine showed release and absorption of the nitroglycerine through the skin.

Furthermore, DIMAC matrix containing nitroglycerine, when taken orally, is capable of providing extended duration release of the embodied nitroglycerine.

EXAMPLE 2

In a preliminary study, eleven formulations of DIMAC containing 10–20 w/w% of diltiazem hydrochloride (DTZ) or urapidil fumerate (UPD) were prepared and assessed for potential use as a matrix for drug storage and release of the embodied drug in a sustained duration pattern. The appraisal was based on: (1), ease of mixing; (2), fluidity of the slurry for capsule filling; (3), set-up time and working time; (4), cure time; (5), consistency of matrix gel after cure; and (6), appearance of the residual matrix gel delivery system after dissolution of the gelatin capsule.

Formulation

| # | Percentages (w/w %) of Components | | | |
|---|-------|-----|------|-----|
|   | PHEMA | PEG | DMSO | DTZ |
| 1 | 30 | 45 | 5 | 20 |
| 2 | 25 | 50 | 5 | 20 |
| 3 | 25 | 45 | 10 | 20 |
| 4 | 30 | 40 | 10 | 20 |
| 5 | 20 | 50 | 10 | 20 |
| 6 | 25 | 55 | 10 | 10 |

-continued

| # | Percentages (w/w %) of Components | | | |
|---|---|---|---|---|
| | PHEMA | PEG | DMSO | |
| 7 | 30 | 55 | 5 | 10 |
| 8 | 25 | 60 | 5 | 10 |
| 9 | 25 | 55 | 5 | 15 UPD |
| 10 | 30 | 50 | 5 | 15 |
| 11 | 25 | 55 | 5 | 15 |

Procedure

All mixing was performed on ice (0°–16° C.) in order to keep the slurry at its lowest viscosity to enhance flow and thereby facilitate the filling of the gelatin capsules.

The order of component mixing was: (1), add the loading drug to PHEMA; (2), blend in the PEG; and (3), lastly mix in the DMSO. While the prepared slurry is maintained on ice, withdraw 2–3 cc through a plastic cannula connected to a 3–5 cc plastic syringe. After wiping the tip of the cannula, discharge appropriate amounts of slurry and completely fill the larger compartment of the open and upright part of the gelatin capsule. The upright-positioned smaller part of the gelatin capsule was also filled to ⅓ of its capacity. Solidification (set-up) was allowed to progress for 15-minutes before rejoining the capsule compartments. The "cure" phenomena follows set-up and is virtually complete within 2–4 hours after pour. After this time, it is not possible to separate the capsule compartments without tearing of the matrix gel, although reuniting occurs readily because of the adherent quality of the cured matrix gel.

Results:

In-vitro

Dissolution of the gelatin capsular cover occurred within 15–30 minutes when the drug loaded DIMAC matrix system in a gelatin capsule was stirred in a volume of warm water. the capsular shaped DIMAC matrix system maintained its form while stirring continued over the next 8-hours, although the outside surface loses its adherence and also becomes soft.

Of the formulations examined, capsule numbers 3, 7, and 11 were determined as being mechanically most suitable for use in future development and evaluation studies.

EXAMPLE 3

In-vivo

DIMAC synthetic resin matrix system embodied with diltiazem hydrochloride (DTZ) or urapidil (UPD), prepared in gelatin capsules, was evaluated as an oral delayed and sustained delivery system in conscious dogs.

Formulations

| | I. DIMAC/DTZ (15%) | | | |
|---|---|---|---|---|
| 25% PHEMA | 55% PEG | 5% DMSO | | 15% DTZ |
| | II. DIMAC/UPD (10%) | | | |
| 25% PHEMA | 60% PEG | 5% DMSO | | 10% UPD |
| | III. DIMAC | | | |
| 38% PHEMA | 57% PEG | 5% DMSO | | |

Approximately 75 uCi of isotopically labelled DTZ or UPD was blended into their respective slurry prior to filling the gelatin capsule. The isotopically labelled compositions were allowed to set-up prior to rejoining the filled upper and lower capsule compartments. Curing proceeded overnight, with animal dosing performed at 8:00 a.m. the following morning. The control DIMAC matrix samples without drug were prepared in an identical manner.

Six conscious dogs, three males and three females, one of each sex in three treatment groups were used in this study. The oral dose of DTZ was 30 mg/kg, while that for UPD was 10 mg/kg.

Blood samples were drawn at 0-time immediately prior to dosing, and at 0.5, 1.0, 2.0, 4.0, 6.0, 8.0, 24, and 32 hours after oral administration of the three test preprations. One ml of plasma, suitably prepared was counted for 5-minutes for level of radioactivity (dpm).

Results

The results in DPM/ml are reported in the following table:

| TIME | DIMAC | UPD | DTZ |
|---|---|---|---|
| 0.0 hr | 34 | 35 | 32 |
| 0.5 | 36 | 330 | 78 |
| 1.0 | 36 | 406 | 190 |
| 2.0 | 32 | 454 | 442 |
| 4.0 | 38 | 392 | 1020 |
| 6.0 | 36 | 359 | 1003 |
| 8.0 | 34 | 397 | 942 |
| 24.0 | 34 | 84 | 370 |
| 32.0 | | 24 | 242 |

Conclusions:

1. DTZ released from the DIMAC matrix reached a peak plasma level at 4-hours after oral dosing and maintained this level throughout the first 8-hour evaluation. At 24-hour post-oral administration, the plasma isotope concentration had diminished by sixty percent (60%), and continued to decline over the next 8-hours (note that the isotope level at 32-hours was still 10 times greater than background.) Calculations relating the blood plasma dpm determinations to the initial oral dose of the isotopically labelled DTZ indicated that peak DTZ plasma level was equivalent to approximately ⅓ of the administered does, and that greater than 50% of this dose was released during the 8-hour period after oral administration.

2. UPD release from the DIMAC matrix was apparent at 0.5 hour after administration and reached a peak plasma radioactivity at the 2-hour sampling, although insignificant diffrences between the values occurred throughout the 8-hour sampling period. Marked reduction in the plasma concentrations were seen at the 24- and 32-hour sampling. Calculations estimating the percent of UPD released from the DIMAC matrix sustained delivery system suggested that at least 50% of the labelled drug was released during the 8-hour observation period.

EXAMPLE 4

Determination was made of the release characteristics of the DIMAC synthetic resin matrix system embodied with the drug diltiazem hydrochloride (DTZ) following oral administration to conscious dogs. Absorption patterns of the drug from the DIMAC matrix were compared with those obtained from a solution of the drug also administered orally. C14 DTZ was used to assess the amount of radioactivity released from DIMAC matrix into the plasma and urine of the test animals, and total radioactivity of the drug released from DIMAC matrix in plasma and urine was quantitated. The relative bioavilability and pharmacokinetic parameters for the two oral doage forms of DTZ were then determined and compared.

Formulation:

The DIMAC matrix containing DTZ, composed of radioactive and non-radioactive components, was prepared as described in EXAMPLE 3. The DIMAC matrix embodied with DTZ had the following formulation (w/w%)

25% PHEMA: 55% PEG: 5% DMSO: 15% DTZ

The radiolabelled DTZ (586 UCi) was micronized and blended into the DIMAC slurry prior to injecting the slurry into the gelatin capsule compartments according to established procedures.

Procedure:

DIMAC matrix embodied with DTZ in gelatin capsules was administered orally according to the dose level and body weight of the dog. This was a crossover study with each dog receiving both the DIMAC matrix and the oral dosing solution. The DTZ dose administered in the DIMAC matrix was 30 mg/kg, while the solution dose was 20 mg/kg. The dogs were fasted for 16 hours prior to dosing and food was withheld until six hours after dosing. Blood was collected at 0, 30, 60 minutes, and at 2, 4, 6, 8, 10, 24, 32, 48, and 72 hours after dosing. The volume of urine output collected was measured and recorded. The radioactivity of C14 DTZ in the plasma and urine samples were measured. The level of DTZ equivalents in the plasma samples was presented as micrograms equivalent per milliliter of plasma, calculated upon the specific activity of the DTZ in both preparations.

The derived pharmacokinetic parameters included: 1, time for the maximum concentration to be reduced by ½ (t-½); 2, area under the plasma concentration curve (AUC); 3, maximum plasma concentration (C-max); 4, time to reach C-max (t-max); 5, mean resident time (MRT); and 6, percent of recovery of administered H3 dose in urine in 72 hours (U%). The summarized results presented below, express the percent change difference in the measured and derived values between the DIMAC matrix DTZ and solution preparations.

| PERCENT CHANGE OF DIMAC FROM SOLUTION CONTROL | | | | | |
|---|---|---|---|---|---|
| t½ | AUC | C-max | t-max | MRT | U % |
| +80 | +59 | +14 | +122 | +30 | +2 |

Although these results revealed a statistically significant increase in t-max, AUC, and MRT over their solution control values, the magnitude of the delayed and extended duration release indices were far less than that obtained in the comparable study presented in EXAMPLE 3. These differences in amplitude of the pharmacokinetic measures were attributed to the formulation procedure employed here in EXAMPLE 4, of the micronizing the radiolabelled tracer prior to blending into the matrix resin slurry. In the earlier study the radiolabelled DTZ was presented into the slurry in an aggregated or clumpy condition. Thus, the process of micronizing resulted in a marked increase in surface area enabling a more rapid dissolution and release from the DIMAC matrix and subsequently exhibiting a rate of absorption, although somewhat delayed, more similar to that observed following the oral administration of the solution control.

EXAMPLE 5

Here, determination was made of the release characteristics of the DIMAC synthetic resin matrix system embodied with the drug urapidil fumerate (UPD) following oral administration to conscious dogs, in an identical procedure to that described in EXAMPLE 4.

Formulation:

The DIMAC matrix containing UPD, composed of radioactive and non-radioactive components, was prepared as described in EXAMPLE 3. The following DIMAC matrix with the UPD was prepared (w/w%):

25% PHEMA:60% PEG:5% DMSO: 10% UPD

In this study, 621 uCi of C14 UPD was micronized and blended into the slurry at the time the DIMAC matrix with UPD was prepared. The UPD dose administered in DIMAC matrix was 10 mg/kg, and the same dose was used in the control solution. The bioavailability and pharmacokinetic derivatives were expressed as percent change difference in values between the DIMAC matrix UPD and the UPD solution preparations.

| PERCENT CHANGE OF DIMAC FROM SOLUTION CONTROL | | | | | |
|---|---|---|---|---|---|
| t½ | AUC | C-max | t-max | MRT | U % |
| +40 | −31 | −156 | +346 | +69 | +8 |

Although these results revealed a statistically significant change in C-max, t-max, MRT, and t-½ over their solution control values, the magnitude of the delayed and extended druation release indices were far less than that obtained in the comparable study presented in EXAMPLE 3. These differences in amplitude of the phamacokinetic mreasures was attributed to the formulation procedure employed here in EXAMPLE 5, of micronizing the radiolabelled tracer prior to blending into the matrix resin slurry. In the earlier study the radiolabelled UPD was presented into the slurry in an aggregated or clump condition. Thus, the process of micronizing resulted in a marked increase in surface area enabling a more rapid dissolution and release from the DIMAC matrix and subsequently exhibiting a rate of absorption, although somewhat delayed, more similar to that observed following the oral administration of the solution control.

EXAMPLE 6

Examination of the effectiveness of DIMAC synthetic resin matrix to serve as a drug storage and extended duration oral delivery system for the drug cimetidine (CMD) was examined in conscious dogs using an experimental procedure described in EXAMPLES 4 and 5.

The DIMAC matrix containing CMD was prepared as described in EXAMPLE 3, the micronized radiolabelled CMD (66.5 uCi) added to the DIMAC matrix slurry during the preparation of the DIMAC matrix filled gelatine capsule formulation, comprised of the following components:

25% PHEMA:55% PEG:5% DMSO:15% CMD

The CMD dose administered to conscious dogs in the configuration of DIMAC matrix in gelatin capsules was 45 mg/kg, the same dose was administered in the control solution. The findings of this experiment are summaraized in the following table:

| PERCENT CHANGE OF DIMAC FROM SOLUTION CONTROL | | | | | |
|---|---|---|---|---|---|
| t½ | AUC | C-max | t-max | MRT | U % |
| +97 | +32 | −34 | +75 | +87 | +9 |

It should be quite obvious from reviewing the above examples that the synthetic resin matrix system for this invention, and particularly for use for drug storage and for extended duration drug release, can be used for a variety of therapeutic treatments. For example, the medicament agent selected from pharmacological classes of drugs can be used in the treatment of illnesses in the nature of antimicrobial, antibiotic, analgesic, anticonvulsant, antipsychotic, hormone needs, antihistamine, cardiovascular, anxiolytic, antispasmodic, skeletal muscle relaxants, antiviral, antineoplastic, diuretic, antiparasitic, healing enhancers, respiratory, and learning and memory enhancers.

The following chart indicates an example of the type of drugs that are currently known for usage for the treatment of medical problems associated with the foregoing categories.

| TREATMENT CATEGORIES | |
|---|---|
| | DRUGS PRESCRIBED |
| Antimicrobial: | silver sulfadiazine, nitrofurazone, and antibiotics |
| Analgesic: | codeine |
| Anticonvulsant: | phenytoin |
| Antipsychotic: | trifluoperazine or amitriptyline |
| Hormones: | corticosteroids |
| Antihistamine: | diphenhydramine |
| Cardiovascular: | diltiazem, nitroglycerine, or propranolol |
| Anxiolytic: | diazepam, or chlordiazepoxide |
| Antispasmodic: | oxybutynin |
| Skeletal muscle relaxant: | diazepam |
| Antiviral: | acyclovir |
| Antineoplastic: | methotrexate |
| Diuretic: | hydrochlorothiazide |
| Antiparasitic: | lindane |
| Respiratory: | theophylline |
| Learning and memory enhancers: | ergoloid mesylates |

BRIEF DESCRIPTION OF THE DRAWINGS

In referring to the drawings, FIG. 1 discloses in perspective view a performed wound or other type of dressing of the present invention as it is applied to a treated surface, such as a surface of the skin of a human or animal, with a backing sheet covering the dressing material and showing it in a partially peeled-away condition;

FIG. 2 discloses an isometric view of an encapsulated form of this invention;

FIG. 3 discloses an exploded view of the encapsulated form of this invention as shown in FIG. 2;

FIG. 4 is a transverse sectional view taken along the line 4—4 of FIG. 3;

FIG. 5 discloses the embodiment of this invention within a spherical gelatin capsule; and FIG. 6 discloses the encapsulation of this invention within a suppository.

DESCRIPTION OF THE PREFERRED EMBODIMENTS

Generally, the synthetic wound dressing, and extended delivery of drugs system, of the present invention, comprises a resin of varying concentrations of biologically compatible, non-toxic, hydrophyllic, water insoluble, water swellable polymer, such as those as listed earlier in this application. This component was generally referred to as PHEMA. The polymer of this invention may include hydroxy($C_2$–$C_4$-alkyl) methacrylate, hydroxy($C_2$–$C_4$alkyl) acrylate, hydroxy($C_2$–$C_4$alkoxy$C_2$–$C_4$alkyl) methacrylate, hydroxy($C_2$–$C_4$alkoxy$C_2$–$C_4$alkyl)acrylate, alkoxy($C_2$–$C_4$alkoxy$C_2$–$C_4$alkyl)methacrylate, alkoxy($C_2$–$C_4$alkoxy$C_2$–$C_4$alkyl) acrylate, N-($C_1$–$C_4$alkyl) acrylamide, N-($C_1$–$C_4$alkyl) methacrylamide, N,N-di($C_1$–$C_4$alkyl) acrylamide, N,N-di($C_1$–$C_4$alkyl) methacrylamide, vicinal-epoxy($C_1$–$C_4$alkyl) methacrylate, or vicinal-epoxy($C_1$–$C_4$alkyl) acrylate. Additionally, the resin comprises an inert, water soluble, organic liquid solvent, previously generally identified as PEG. A hydrogen binding plasticizer additive, such as dimethylsulfoxide, is also included, and was previously referred to as the DMSO ingredient. It has been found that the formulation of the resin of this invention, consisting essentially of PHEMA, PEG, and DMSO, and referred to collectively as DIMAC, can be altered so as to control the set-up time of the resin from almost simultaneous with mixing (e.g., several seconds) up to about 45 minutes, or longer, depending on the relative concentration of the ingredient DMSO.

Where the composition is utilized as a wound dressing, or for other delivery of drugs to the surface of the human body, or that of an animal, or the like, the dressing bandage in an already adherent state is applied to the body, rather than as a spreadible paste. More specifically, in referring to FIG. 1, the preformed dressing is illustrated in its entirety by reference character 1. This preformed dressing 1 is shown to comprise a substrate 3, preferably of a biaxially stretchable fabric-like material. For example, such a bidirectional stretchable material made of nylon or Lycra is available from Tweave, Inc., of Norton, Mass., under the trade designation or style No. 901. A layer of the stretchable wound dressing 1 of the present invention is applied to the front face of the substrate 3 with the layer of synthetic wound or other form of dressing being indicated by reference character 5. To protect the dressing coating 5 applied to substrate 3 prior to usage, and to maintain it in an aseptic condition, a plastic film backing sheet 7 is applied to the synthetic wound dressing coating 5 and is slightly adhered to substrate 3. As shown in FIG. 1, prior to usage, the backing sheet 7 is peeled from the dressing so as to expose the dressing coating 5 on the substrate 3, thus making the bandage or dressing ready for application to the skin surface, for whatever form of treatment is required. Substrates 3 and 7 may extend beyond the wound dressing 5 to provide a non-adhesive tab permitting easy handling of the dressing after removal of the cover film 7 without touching the active sticky surface 5.

While the inclusion of the DMSO plasticizer as a component of the formulation of the synthetic resin dressing of the present invention has heretofore been described as primarily aiding in giving predictability to the set-up time of the synthetic resin dressing, it has been found, even in the case of preformed dressing bandages, such as shown in FIG. 1, that the inclusion of DMSO (or other plasticizers) as a component of the formulation for the synthetic resin wound dressing coating 5 on the bandage, has a beneficial effect in that it is believed that the DMSO plasticizer results in a solidification or curing of the polymer system of the synthetic resin dressing such that there is a progressive gelling of the resin mixture preceding the actual set-up of the mixture. The term "set-up" is defined as the time between the mixing of the components of the synthetic resin wound dressing into a paste and the time an occlusive, non-tacky film appears on the surface of the paste with little or no adhesivness to the touch. Generally, at the time of set-up, the resin will still have a pliable consistency. When no drug or medicament has been added, the paste in its "set-up" condition will have a semi-opaque character.

Then, depending on the relative concentration of the components of the synthetic resin system, a progressively developing transparency of the resin film will result with an increase in the elasticity and rebound of the resin, and the surface of the resin will generally have a significantly increased surface adhesiveness resulting from the reactions of the added DMSO. Generally, these last-described changes and physical characteristics of the resin system require about 5 to 10 times longer to develop than is required for the initial "set-up" to occur. This delay process of developing a transparent film with an increase in elasticity, rebound and surface adhesiveness is referred to as curing.

Further, in accordance with the broader aspects of this invention, as defined in this application, the concept of this invention in combining the PHEMA, the PEG, and the DMSO, in addition to various active medicaments, may be incorporated within either the bandage or covering material itself, as shown in FIG. 1, or in the alternative, the concept of this invention may be embodied within an encapsulated form. For example, FIGS. 2 through 4 disclose a gelatin capsule 9, generally formed of a pair of capsule components 11 and 13, of the usual construction as well known in the trade, but in this particular instance, the composition of this invention will be poured therein when initially mixed, and still in its flowable state, controlled by the quantity of DMSO added so as to become a DIMAC matrix 15 encapsulated within the capsule 9, and have the various drug particles 17 embedded therein, as of the type as defined within this particular invention. Thus, the time delayed release of the drug particles into the body system is effected in a manner as previously described in this application, its timing depending upon either the solubility or moisture permeability, or dissolvable of the capsule, and also the matrix 15 until the gastric or other body fluids attains exposure to the drug particles, and effects their solubility for delivery to the biological system.

In addition, the concept of this invention can be contained within encapsulated spheres, as shown in FIG. 5, wherein the spherical covering material 19 may likewise be formed of the usual gelatin material of the type that is either soluble, dissolvable, or permeable, all as readily available in the art. Then, the DIMAC matrix 21 will be contained within the formed spheroid capsules, and incorprate the drug particles 23 therein, and for timed release to the body system.

In addition, it might also be commented that the concept of this invention, particularly in the manner as explained within this FIG. 5, may likewise be used for purposes other than for the treatment of wounds or illnesses of the body, and for example, DIMAC embedded herbicides and insecticides could possibly be included within spherical components, such as that shown in FIG. 5, for delivery to crops, or the like, and for use for insecticidal, herbicidal, or even fertilizing purposes. These are examples as to how the subject matter of this invention may be employed within other delivery systems, for providing a timed delay release of their active components, such as when exposed to other moisture deriving components, such as the moist ground, or to rainfall, or to other humidity, for the timed delay release of their active components for the treatment of some other surface, such as crops, the ground, or the like.

In addition to the foregoing, as can be seen in FIG. 6, the subject matter of this invention may be used in suppository form. For example, the usual suppository capsule 25, as readily available in the art, usually formed of some form of dissolvable gelatin, may have encapsulated therein the DIMAC matrix 27 of this invention, and have the active ingredients comprising the drugs 29 embodied therein, to provide for their timed delayed release to the body system, in the usual manner that drugs are currently delivered to the body through the use of a suppository-like delivery system.

These are just examples of various physical methods for structurally encapsulating the subject matter of this invention, for providing for the times delayed release of the active components to some biological system for treatment.

Variations or modifications to the subject matter of this disclosure may occur to those skilled in the art upon reviewing the summary and description of this invention. Such variations and modifications, if within the spirit of this invention, are intended to be encompassed within the scope of any claims to patent protection issuing upon this invention. The description of the preferred embodiments as set forth herein is done so principally for illustrative purposes only.

Having thus described the invention what is claimed and desired to be secured by Letters Patent is:

1. A synthetic resin matrix system for drug storage and extended duration drug release comprising a particulate, hydrophilic, water swellable polymer, an inert, non-toxic water miscible organic solvent, and a hydrogen bonding plasticizer, said polymer selected from the group consisting of hydroxy($C_2$–$C_4$-alkyl) methacrylate, hydroxy($C_2$–$C_4$alkyl) acrylate, hydroxy($C_2$–$C_4$alkoxy$C_2$–$C_4$alkyl) methacrylate, hydroxy($C_2$–$C_4$alkoxy$C_2$–$C_4$alkyl) acrylate, alkoxy($C_2$–$C_4$alkoxy$C_2$–$C_4$alkyl) methacrylate, alkoxy($C_2$–$C_4$alkoxy$C_2$–$C_4$alkyl) acrylate, N-($C_1$–$C_4$alkyl) acrylamide, N-($C_1$–$C_4$alkyl) methacrylamide, N,N-di($C_1$–$C_4$alkyl) acrylamide, N,N-di($C_1$–$C_4$alkyl) methacrylamide, vicinal-epoxy($C_1$–$C_4$alkyl) methacrylate, or vicinal-epoxy($C_1$–$C_4$alkyl) acrylate, said solvent selected from the group consisting of polyethylene glycol or polypropolene glycol having a molecular weight averaging between about 200–2000 gram molecules weight units, and wherein said plasticizer being selected from the group consisting of dimethylsulfoxide, dimethylphthalate, 2,3-butylene carbonate, dimethylformamide, dimethyltetramethylene sulfone, diethylsulfone, methylene glycolate, methylpropyl sulfone, or butyrolactone, with said polymer ranging between about 15%–50% by weight of said matrix system, with said solvent ranging between about 30%–65% by weight of said matrix system, and with said plasticizer ranging up to about 20% by weight of said matrix system.

2. A synthetic resin matrix system for drug storage and extended duration drug release as set forth in claim 1, wherein the preformed configuration of the matrix system allows for the administration of the matrix system to ailing animals or humans by different modes of application including one of oral, rectal, topical, sublingual, subcutaneous implant, and organ-specific placement.

3. A synthetic resin matrix system for drug storage and extended duration drug release as set forth in claim 1, further comprising a medicament agent for local or systemic therapeutic effects, said medicament agent from pharmacological classes of drugs such as antimicrobial, antibiotic, analgesic, anticovulsant, antipsychotic, hormone, antihistamine, cardiovascular, anxiolytic, antispasmodic, skeletal muscle relaxant, antiviral, antineoplastic, diuretic, antiparasitic, healing enhancer, respiratory, and learning and memory enhancers.

4. A synthetic resin matrix system for chemical storage and extended duration release as set forth in claim 1, wherein the prefabricated configuration of the matrix system allows for the administration of the matrix containing agriculture products, particularly herbicides, insecticides, or nutritional supplements.

5. A synthetic resin matrix system for drug or chemical storage as set forth in claim 1, wherein the release rate of the embodied drug or chemical is controlled by the particle size, and its surface area, or the embodied active agent in a manner such that large embodied particles having small surface area are released at a slower rate than smaller particles with relatively larger surface area.

6. The invention of claim 3 and wherein said included drugs comprising of silver sulfadiazine, nitrofurazone, hydrocortisone, hydrocortisone acetate, and hydrocortisone sodium succinate, nitroglycerine, diltiazem hydrochloride, urapidil fumerate, urapidil, and cimetidine.

7. The invention of claim 6 and wherein said drug synthetic resin matrix system being encapsulated.

* * * * *